United States Patent [19]
Mueller et al.

[11] Patent Number: 5,189,038
[45] Date of Patent: Feb. 23, 1993

[54] METHOD OF STIMULATING SUPEROXIDE GENERATION

[75] Inventors: Richard A. Mueller, Glencoe; Akira Nakao, Skokie; Richard A. Partis, Evanston, all of Ill.

[73] Assignee: G. D. Searle and Co., Chicago, Ill.

[21] Appl. No.: 724,680

[22] Filed: Jul. 2, 1991

Related U.S. Application Data

[62] Division of Ser. No. 579,458, Sep. 7, 1990, Pat. No. 5,082,854.

[51] Int. Cl.$^5$ .................................... A61K 31/495
[52] U.S. Cl. .................................................. 514/255
[58] Field of Search ........................................ 514/255

[56] References Cited

U.S. PATENT DOCUMENTS

| | | |
|---|---|---|
| 4,029,812 | 6/1977 | Wagner ................. 514/346 |
| 4,076,841 | 2/1978 | Wagner ................. 514/346 |
| 4,078,084 | 3/1978 | Wagner ................. 514/346 |
| 4,663,333 | 5/1987 | Mueller ................. 514/346 |
| 4,857,558 | 8/1989 | Mueller ................. 514/346 |

FOREIGN PATENT DOCUMENTS

| | | |
|---|---|---|
| 0190682 | 1/1986 | European Pat. Off. . |
| 0190685 | 1/1986 | European Pat. Off. . |
| 0232089 | 8/1987 | European Pat. Off. . |
| 1936463 | 2/1971 | Fed. Rep. of Germany . |
| 59-222438 | 12/1984 | Japan . |
| 61-024536 | 2/1986 | Japan . |
| 61-043132 | 3/1986 | Japan . |
| 1557622 | 12/1979 | United Kingdom . |

OTHER PUBLICATIONS

Cross, C. E., et al., "Oxygen Radicals and Human Disease," Ann. Int. Med., 107:526-545 (1987).
Ward, P. A., "Oxygen Radicals, Inflammation, and Tissue Injury," Free Radical Biology & Medicine, 5:403-408 (1988).
Shepard, V. L., "The Role of the Respiratory Burst of Phagocytes in Host Defense," Semin. Respir. Infect., 1(2):99-106 (1986).
Kukreja, R. C., et al., "PGH Synthase and Lipoxygenase Generate Superoxide in the Presence of NADH or NADPH," Circulation Research 59(6):612-619 (1986).
Katayama, K., et al., Agents and Actions, 21(3/4):269-271 (1987).
Biemond, P., et al., Scand. J. Rheumatology, 19:151-156 (1990).
Kreutner, W., et al., J. Pharmacol. Exp. Ther., 247(3):997-1003 (1988).
Concetti, M., et al., Clinical Rheumatology, 9(1):51-55 (1990).
Auer, D. E., et al., J. Vet. Pharmacol. Therap., 13(1):59-66 (1990).
Kanofsky, J. R., Chem. Biol. Interactions, 70:1-28 (1989).

*Primary Examiner*—S. J. Friedman
*Attorney, Agent, or Firm*—Mary Jo Kanady; Paul D. Matukaitis

[57] ABSTRACT

The present invention is directed to a method of stimulating superoxide generation using phenolic thioethers which stimulate the generation of superoxide.

6 Claims, No Drawings

METHOD OF STIMULATING SUPEROXIDE GENERATION

This is a division of application Ser. No. 07/579,458, filed Sep. 7, 1990 now U.S. Pat. No. 5,082,854.

BACKGROUND OF THE INVENTION

1. Field of the Invention

The present invention is directed to a method of stimulating superoxide generation using phenolic thioethers which stimulate the generation of superoxide.

2. Background Information and Related Art

Recently, oxygen radicals have been implicated in the pathogenesis of many diseases. This implication is reflected by the many conferences devoted to this topic, books on the subject of free radicals and disease, and the appearance of two new specialized journals: *Free Radical Research Communications,* and *Free Radical Biology and Medicine.*

Much is known about the physicochemical properties of the various oxygen radicals, but knowledge of their overall importance in the initiation and amplification of human disease is limited. Some clinical conditions in which oxygen radicals are thought to be involved are discussed in Cross, C. E., et al., "Oxygen Radicals and Human Disease," ANN. INT. MED., 107:526-545 (1987) (see Table 1, p. 527) and Ward, P. A., et al., "Oxygen Radicals, Inflammation, and Tissue Injury," FREE RADICAL BIOLOGY & MEDICINE, 5:403-408 (1988). Among the clinical conditions in which oxygen radicals are thought to be involved are, for example, inflammatory-immune injury, autoimmune diseases, ischemia-reflow states, aging disorders, cancer, cigarette-smoke effects, emphysema, acute respiratory distress syndrome (ARDS), atherosclerosis, rheumatoid arthritis, senile dementia, cataractogenesis, retinopathy of prematurity, and contact dermatitis.

Oxygen radicals are capable of reversibly or irreversibly damaging compounds of all biochemical classes, including nucleic acids, protein and free amino acids, lipids and lipoproteins, carbohydrates, and connective tissue macromolecules. These species may have an impact on such cell activities as membrane function, metabolism, and gene expression. Oxygen radicals are formed in tissues by many processes (see Cross, et al., p. 528, Table 2). These are believed to be both endogenous, such as mitochondrial, microsomal and chloroplast electron transport chains; oxidant enzymes such as xanthine oxidase, indoleamine dioxygenase, tryptophan dioxygenase, galactose oxidase, cyclooxygenase, lipoxygenase, and monoamine oxidase; phagocytic cells such as neutrophils, monocytes and macrophages, eosinophils, and endothelial cells; and antioxidation reactions; and exogenous, such as redoxcycling substances, drug oxidations, cigarette smoke, ionizing radiation, sunlight, heat shock and substances that oxidize glutathione. They may be involved in the action of toxins such as paraquat, cigarette smoke, and quinone antitumor drugs.

Generation of reactive oxygen species is a critical event in successful host defense against invading organisms. Both neutrophils and macrophages rely on a variety of oxidants to damage bacterial constituents (see V. L. Shepherd, "The role of the respiratory burst of phagocytes in host defense," SEMIN. RESPIR. INFECT. (United States) June 1986, 1(2) p. 99-106.

Various thioether compounds have been described previously. For example, U.S. Pat. No. 4,663,333 discloses compounds of the formula

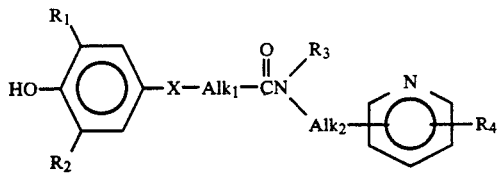

wherein: $R_1$ and $R_2$ are the same or different members of the group consisting of halo, phenyl, substituted phenyl and a

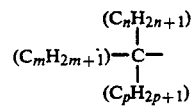

group wherein n, m and p are independently an integer of from 1 to 8 provided n+m+p is equal to or less than 10; X is thio, sulfinyl or sulfonyl; $Alk_1$ is straight or branched chain lower alkylene of 1 to 6 carbon atoms, $R_3$ is lower alkyl, $Alk_2$ is straight or branched chain alkylene of 1 to 4 carbon atoms; $R_4$ is selected from the group consisting of hydrogen halo, hydroxy, lower alkyl and lower alkoxy; and the pharmaceutically acceptable salts there of. The compounds inhibit 5-lipoxygenase and are useful in the treatment of inflammation, allergy and hypersensitivity reactions and other disorders of the immune system.

Wagner, et al. U.S. Pat. No. 4,029,812, and related U.S. Pat. Nos. 4,076,841 and 4,078,084 which issued from divisional applications of the -812 application, all assigned to The Dow Chemical Company, disclose 2-(3,5-di-tert-butyl-4-hydroxyphenyl)thiocarboxylic acids, esters and simple amides which are hypolipidemics and are useful in reducing plasma lipid levels, especially cholesterol and triglyceride levels.

European Patent Application EP 0190685 discloses heterocyclic amides represented by the formula

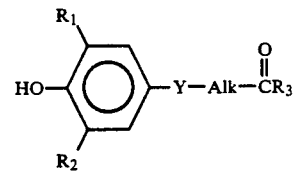

wherein $R_1$ and $R_2$ are the same or different members of the group consisting of halo, phenyl, substituted phenyl and a

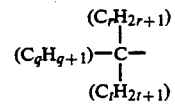

group wherein q, r and t are independently an integer of from 1 to 8 provided that q+r+t is equal to or less than 10; Y is thio, sulfinyl or sulfonyl; Alk is straight or branched chain lower alkylene, and $R_3$ is a heterocyclic amine represented by the formula:

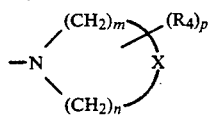

wherein $R_4$ is selected from the group consisting of hydrogen, lower alkyl, phenyl, substituted phenyl, benzyl, substituted benzyl, carboxyl or carboxyloweralkyl; X is selected from the group consisting of N—$R_4$, O and $CH_2$, m is 2 or 3; n is 2 or 3 when X is O or N—$R_4$ and n is 1 to 3 when X is $CH_2$; p is 0 to 2; and the pharmaceutically acceptable salts thereof. The compounds inhibit 5-lipoxygenase and are useful as anti-inflammatory and anti-allergy agents.

European Patent Application EP 0190682 discloses anilides represented by the formula

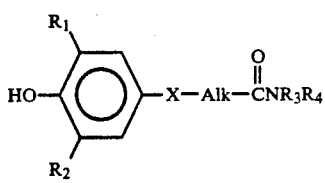

wherein: $R_1$ and $R_2$ are the same or different members of the group consisting of halo, phenyl, substituted phenyl and a

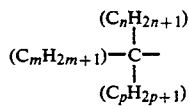

group wherein n, m and p are independently an integer of from 1 to 8 provided that $n+m+p$ is equal to or less than 10; X is thio, sulfinyl or sulfonyl; Alk is straight or branched chain lower alkylene; $R_3$ is hydrogen or lower alkyl; and $R_4$ is phenyl or substituted phenyl. The compounds inhibit 5-lipoxygenase and are useful in the treatment of allergy and hypersensitiviy reactions and inflammation.

U.S. Pat. No. 4,857,588 discloses methods for inhibiting lipoxygenase and includes pharmaceutical formulations comprising a pharmaceutical carrier and an effective lipoxygenase inhibiting amount of a compound of the formula

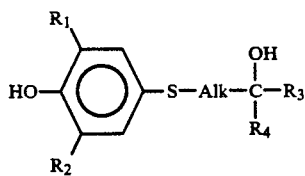

wherein: $R_1$ and $R_2$ are the same or different members of the group consisting of 1,1-dimethylethyl, halo, phenyl and substituted phenyl; Alk is straight or branched chain lower alkylene; $R_4$ is hydrogen or lower alkyl; $R_3$ is hydrogen or lower alkyl or a cycloalkyl group of from 3 to 8 carbon atoms. The disclosed compounds inhibit 5-lipoxygenase and are useful in the treatment of allergy and hypersensitivity reactions and inflammation.

United Kingdom Patent No. 1,557,622 discloses 3,5-di-tertiary-butyl-4-hydroxyphenyl pyridine compounds of the formula:

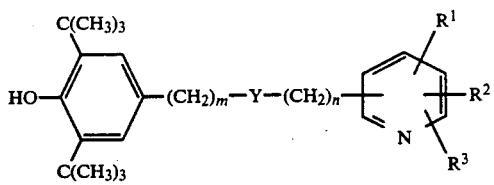

or a pharmaceutically acceptable acid addition salt thereof, wherein:
  y is —O—, —S— or —N($R^4$)— [wherein $R^4$ is a hydrogen atom, an alkyl group having 1 to 4 carbon atoms (e.g. methyl, ethyl, propyl or butyl), an aralkyl group (e.g. benzyl, methoxybenzyl or phenethyl)];
  each of $R^1$ and $R^2$ is a hydrogen atom, a hydroxyl group or an alkyl group having 1 to 4 carbon atoms (e.g. methyl, ethyl, propyl or butyl);
  $R^3$ is a hydrogen atom, a hydroxymethyl group or a group of the formula:

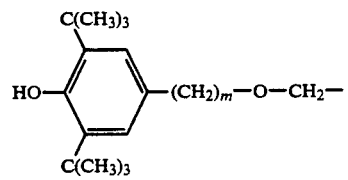

m is 0 or 1; and
n is 0, 1, 2 or 3.

Preferable compounds of the formula are those wherein Y is —O— or —N($R^4$)— (wherein $R^4$ is as defined above). These compounds are said to have antiatherosclerotic, antihyperlipidemic, cerebral vasodilating and antithrombotic activities, and are useful as drugs for the treatment of eschemic vascular diseases in mammals such as atherosclerosis, cardiac infarction, angina pectoris, cerebral infarction, cerebral hemorrhage, renal infarction, intermittent claudication, transient cerebral attack or thrombosis.

German Offenlegunsschrift 1 936 463 discloses phenols having the formula

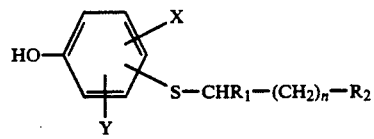

in which
  X and Y, which may be the same or different, stand for hydrogen or halogen atoms or lower alkyl radicals,
  $R_1$ stands for a hydrogen atom or a lower alkyl radical,
  $R_2$ stands for one of the groups,

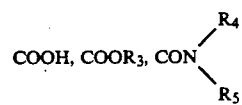

CN, and, in case n equal 0 and $R_1$ is a hydrogen, it can only be $C_6H_5$ and in case n equal 1, it can also be OH, whereby $R_3$ stands for an alkyl radical with 1 to 5 carbon atoms and $R_4$ and $R_5$, which may be the same or different, stand for hydrogen atoms, lower or medium alkyl radicals or, together with the nitrogen atom, stand for a ring that may contain another heteroatom, n stands for 0 or 1 as well as with the corresponding phenolates. The phenols are said to have biocidal activity but they are said to be above all suitable as intermediates for the preparation of biocidal substances, for example, phosphate esters and carbamates.

SUMMARY OF THE INVENTION

The present invention relates to a method of stimulating superoxide generation which comprises administering to a mammal in need of such treatment an amount of a compound of the Formula I

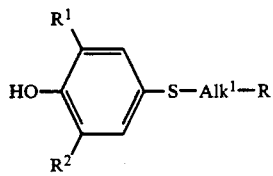

or a pharmaceutically acceptable salt or steroisomer or geometric isomer thereof; wherein $R_1$ and $R_2$ are the same or different and independently represent tert-alkyl or phenyl;

$Alk^1$ represents straight or branched chain alkylene of 1 to 10 carbon atoms; and R represents:
a)

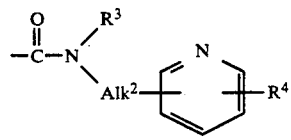

wherein $R^3$ is hydrogen or alkyl of 1 to 4 carbon atoms, $Alk^2$ is straight or branched chain alkylene of 1 to 4 carbon atoms, and $R^4$ is hydrogen or alkyl of 1 to 4 carbon atoms;

b)

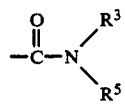

wherein $R^3$ is hydrogen or alkyl of 1 to 4 carbon atoms and $R^5$ is phenyl or substituted phenyl;

c)

wherein $R^6$ is a heterocyclic amine represented by the formula

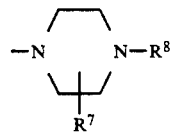

wherein $R^7$ is hydrogen or lower alkyl and $R^8$ is hydrogen, lower alkyl, phenyl, substituted phenyl, benzyl or substituted benzyl; or d)

wherein $R^9$ is hydrogen or alkyl of 1 to 4 carbon atoms and $R^{10}$ is alkyl of 1 to 10 carbon atoms;

which is effective to stimulate superoxide generation.

The compounds of Formula I are stimulators of superoxide generation in neutrophils and may be useful in the therapeutic or prophylactic treatment of disease conditions in which superoxide generation is an important factor.

Although it has been speculated that 5-lipoxygenase may be involved in superoxide generation, the ability of these compounds, which inhibit 5-lipoxygenase, to stimulate superoxide generation in neutrophils indicates that superoxide generation is not governed by 5-lipoxygenase. Thus the activity of the compounds of Formula I in stimulating superoxide generation is not related to the ability to inhibit 5-lipoxygenase.

The present invention provides a method by which neutrophil activation and the generation of superoxide anions are accomplished utilizing the compounds of formula I. Accordingly the compounds of formula I are useful in the design and testing of anti-inflammatory properties of other pharmacologically active agents.

The ability to produce superoxide which may itself be microbocidal or which is then converted to toxic oxidants such as $H_2O_2$, .OH, and singlet oxygen is important to the phagocytic killing mechanisms which enable neutrophils and macrophages to kill bacteria and parasites through phagocytosis.

Therefore, compounds of formula I which stimulate superoxide generation may be useful in the adjunctive therapy of microbial infections. The compounds may also be useful in treating conditions such as Chediak-Higashi Syndrome in which the patient's macrophages and polymorphs are only weakly active causing the patients to suffer from recurring infections involving organisms with normally low pathogenicity. Compounds of formula I may also be useful in the adjunctive therapy of patients whose immune systems have been weakened or impaired by disease or by chemotherapy or radiation therapy and who are more subject to microbial infections.

DETAILED DESCRIPTION OF THE INVENTION

The present invention also relates to a method of stimulating superoxide generation which comprises administering to a mammal in need of such treatment an amount of a compound of the formula

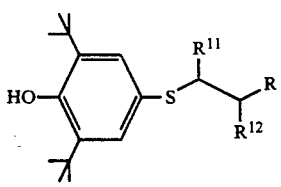

(II)

or a pharmaceutically acceptable salt or steroisomer or geometric isomer thereof, wherein $R^{11}$ and $R^{12}$ are alike or different and are hydrogen or alkyl of 1 to 4 carbon atoms, and R is defined as hereinbefore, which is effective to stimulate superoxide generation.

The term "tert-alkyl" as used herein in reference to $R_1$ and $R_2$ refers to branched chain alkyl moieties of from about 4 to 10 carbon atoms having a tertiary carbon atom attached to the phenyl ring substituted by $R_1$ and $R_2$. Examples of such groups are tert-butyl, i.e., 1,1-dimethylethyl, 1-1-dimethylpropyl, 1-methyl-1-(ethyl)-pentyl, 1,1-diethylpropyl, 1-ethyl-1-(propyl)butyl and the like.

The term "alkylene" refers to straight or branched chain alkylene groups having between about 1 to 10 carbon atoms including, for example, methylene, ethylene, propylene, 1,2-dimethylethylene, pentylene, 1-methylbutylene, isopentylene, neopentylene, etc.

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like The terms "substituted phenyl" and "substituted benzyl" refers to phenyl or benzyl having one or more substituents selected from the group consisting of halo, hydroxy, lower alkyl and lower alkoxy.

Particularly preferred compounds of Formula I are those wherein $R_1$ and $R_2$ are both tert-alkyl.

The expression "pharmaceutically acceptable salts" is intended to include those salts capable of being formed with the compounds of the present invention without materially altering the chemical structure or pharmacological properties thereof. Such salts include inorganic and organic cations or acid addition salts, such as sodium, potassium, calcium, ammonium, alkylammonium, triethanolamine, lysine, hydrochloric, hydrobromide, etc. well known to those skilled in the art. The foregoing salts are prepared in the conventional manner by neutralization of the compounds of Formula I with the desired base or acid.

The compounds of the present invention can be administered in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the particular condition. The effective amount for administration is ordinarily that amount which is required to assure that the mammalian neutrophils involved in the generation of superoxide will be exposed to a sufficient concentration of drug to stimulate the generation of superoxide. A dosage regimen can be effectively determined for each patient or animal by initial intravenous infusion at low dosage level, e.g., 0.01 µg/kg/min and thereafter increasing the dosage until the desired effect is obtained. Thereafter, oral dosages can be determined which will yield equivalent blood levels of drug. Dosages of the compounds of the present invention, will range generally between about 0.1 mg/kg/day to about 100 mg/kg/day and preferably between about 0.5 mg/kg/day to about 50 mg/kg/day. The compounds may also be administered transdermally or topically. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The preparation of the compounds used in practicing the invention has been described in published patents and patent applications, for example, U.S. Pat. No. 4,663,333 incorporated herein by reference describes the preparation of compounds of formula I in which R is an aminoalkylpyridine. U.S. Pat. No. 4,857,588 incorporated herein by references describes the preparation of 4-hydroxyphenylthio alkanols. Other compounds used in the method of the present invention are disclosed in European Patent Applications EP 0190685 and EP 0190682.

BIOLOGICAL EVALUATIONS

The compounds of the invention are evaluated with respect to 5-lipoxygenase inhibition according to the following assay procedure.

Inhibition of 5-lipoxygenase, in vitro:
anti-inflammatory, anti-allergy activities.
The 100,000×g supernatant fraction of Rat Basophilic Leukemia Cell Homogenate (RBL-1) serves as a 5-lipoxygenase enzyme source. The enzyme is incubated with [1-$^{14}$C]-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value (inhibitory concentration to inhibit 50%).

The compounds of the invention are evaluated with respect to superoxide modulating activity according to the following assay procedure:

Human neutrophil superoxide generation: Superoxide generation by formyl-methionyl-leucyl-phenylalanine (FMLP)-stimulated neutrophils was quantitated by the reduction of cytochrome C (Badwey, J. A., Curnutte, J. T. and Karnovsky, M. L., cis-Polyunsaturated fatty acids induce high levels of superoxide production by human neutrophils. *J. Biol. Chem.* 256: 12640–12643, 1981.) To 5 million neutrophils in 2.85 ml of KrebsRinger phosphate buffer, pH 7.2, 50 ul of inhibitor (in 10% DMSO/buffer), and 50 ul ferricytochrome C (5 mM, stock) were added and preincubated for 3 minutes at 37° C. Absorption measurements at 550 nm were recorded at start of preincubation. Fifty ul FMLP (6 uM, stock) was added to initiate reaction. A plateau was reached within 3 minutes and this reading—initial reading (before addition of FMLP) was used to calculate nanomoles of superoxide generated based on a molar extinction coefficient of $2.1 \times 10^4$ cm$^{-1}$mole$^{-1}$.

Isolation of human neutrophils: Human neutrophils were isolated from freshly drawn blood of healthy donors. Two ml of 5% dextran (MW 200,000–300,000) in saline was added to 10 ml aliquots of blood, mixed and placed upright for 45 min. at 37° C. Approx. 8–10 ml of the plasma-white cell suspension from the dextran sedimentation was layered on 3 ml of Ficol-paque in a 15 ml tube and centrifuged at 400 g for 30 min. The supernate, containing plasma and platelets, was discarded by aspiration, and the pellet, containing predominantly neutrophils, was resuspended in 1 ml saline. The suspension was transferred to a clean tube, and pooled with other aliquots of blood treated similarly. The pooled suspension was centrifuged at 350 g for 5 min. and supernate discarded. The pellet was resuspended in 5 ml of 0.05% NaCl with a plastic Pasteur pipette for 25 seconds to lyse contaminating red cells, then 5 ml of 1.75% NaCl added to regain isotonicity. The red cell lysing procedure was repeated, the cells suspended in appropriate buffer (depending on assay) and counted.

For comparison the compound of Formula IV, a known 5-lipoxygenase inhibitor described in U.S. Pat. No. 4,755,524 was used.

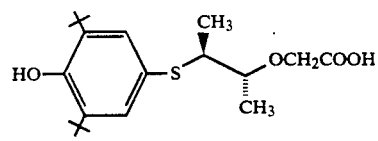

(±)[2S*-[[3.5-bis(1,1-dimethylethyl)-4-hydroxyphenyl]thio]-1R*-methylpropoxy]acetic acid The results with respect to certain compounds of the present invention are set forth in Table I below.

TABLE 1

| Compound Example Number | 5-Lipoxygenase Inhibition IC$_{50}$ (μM) | Stimulation of FMLP Induced Superoxide |
|---|---|---|
| 5 | 0.32 | 5 μM, 50% > control; 10 μM, 227% > control |
| 7 | 0.23 0.33 | Stimulates at 3–20 μM |
| 8 | 0.16 | 5 μM, 150% > control; 10 μM, 206% > control |
| 9 | 0.26 | Stimulates at 5–50 μM |
| 10 | 0.79 | Stimulates at 5–50 μM |
| Formula IV | 4.9 | Inhibited superoxide generation; IC$_{50}$ = 11 μM |

Unlike the compounds of the present invention, the compound of Formula IV inhibited both superoxide generation and 5-lipoxygenase. This data indicates that superoxide generation is not dependent on 5-lipoxygenase and that the ability of a compound to inhibit 5-lipoxygenase is not related to its ability to simulate superoxide generation.

Complement C5a induced superoxide generation is also stimulated by compounds of the present invention.

The following non-limiting examples further illustrate details for the preparation of the compounds used in practicing the present invention. Those skilled in the art will readily understand and appreciate that known variations of the conditions and procedures in the following preparative methods can be utilized. All temperatures are degrees Celsius unless otherwise noted. Melting points were determined on a Thomas-Hoover melting point apparatus and are uncorrected.

EXAMPLE 1

3,5-bis(1,1-dimethylethyl)-4-hydroxyphenyl thiocyanate

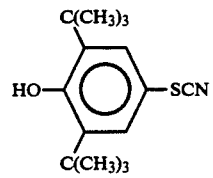

To a three-necked, round bottom 5 L flask, equipped with a mechanical stirrer, gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1 and ½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated by addition of water, filtered and dried for 2 days over phosphorous pentoxide. The resulting gummy yellow solid was recrystallized from pentane and dried in vacuo to yield the product as a white powder, m.p. 61.5°–63° C.

Analysis calc. for $C_{15}H_{21}NSO$:
Theory: C, 68.40; H, 8.03; N, 5.32; S, 12.17.
Found: C, 68.85; H, 8.05; N, 5.29; S, 12.12.

EXAMPLE 2

2,6-bis(1,1-dimethylethyl)-4-mercaptophenol

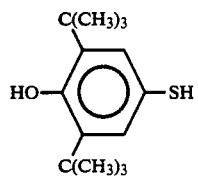

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

N-methyl-N-[2-(2-pyridinyl)ethyl]-2-propenamide

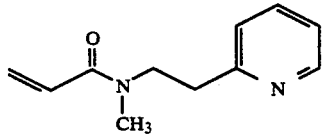

Acryloyl chloride (4.52 g, 0.05 mole) was added dropwise to a stirring solution of triethylamine (30 ml) and 2-(β-methylaminoethyl)pyridine (6.81 g, 0.05 mole) in ethyl ether (500 ml). After stirring overnight at room temperature, the white solid was removed by filtration and washed well with ethyl ether. The organic phases were combined, dried over sodium sulfate, filtered then concentrated to dryness to give an orange oil. The structure was confirmed by NMR.

EXAMPLE 4

3-[[3,5-bis(1,1-dimethylethyl)-4-hydroxy-phenyl]thio]-N-methyl-N-[2-(2-pyridinyl)ethyl]propanamide

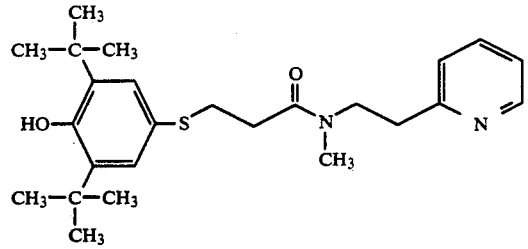

N-methyl-N-[2-(2-pyridinyl)ethyl]-2-propenamide (0.95 g, 0.005 mole) was dissolved in methanol (200 ml) containing 2,6-bis(1,1-dimethylethyl)-4-mercaptophenol (1.19 g, 0.005 mole). After addition of triethylamine (0.5 ml), the solution was stirred at room temperature overnight. The solvent was removed by a nitrogen stream to give a residue which was purified by chromatography on silica to give the title compound, m.p. ca . 82°–84° C.

Anal. calcd. for $C_{25}H_{36}N_2O_2S(428.62)$:
Calc.: C, 70.05; H, 8.47; N, 6.54; S, 7.47.
Found: C, 70.45; H, 8.50; N, 6.60; S, 7.55.

EXAMPLE 5

3-[[3,5-bis(1,1-dimethylethyl)-4-hydroxyphenyl]thio]-N-methyl-N-[2-(2-pyridinyl)ethyl]propanamide monohydrochloride

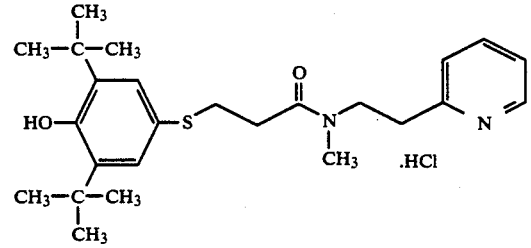

The title compound of Example 4, (2.0 g) was dissolved in ethyl ether (400 ml). With rapid stirring, a saturated solution of hydrogen chloride in isopropyl alcohol was added dropwise until no further precipitation occurred. The oily material was stirred for 20 hours. The ethyl ether was decanted and the residue crystallized from ethyl acetate/ethyl ether to give the title compound (700 mg), m.p. ca . 153°–156° C.

Analysis calc for $C_{25}H_{37}N_2SOCl(465.09)$:
Calc.: C, 64.56; H, 8.02; N, 6.02; Cl, 7.62; S, 6.89.
Found: C, 64.30; H, 7.88; N, 6.00; Cl, 7.79; S, 6.91.

EXAMPLE 6

N-(2,6-dimethylphenyl)-2-propenamide

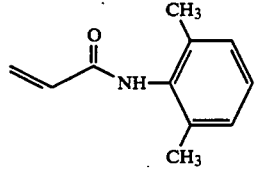

A mixture of 2,6-dimethylaniline (8.68 g, 0.0718 mole) and triethylamine (15.3 ml) in ethyl ether (250 ml) was cooled to +5° C. A solution of acryloyl chloride (6.47 g, 0.0716 mole) in ethyl ether (25 ml) was added dropwise with stirring over a 20 minute period. The solution was allowed to warm to room temperature and stirred for 72 hours. 10 Percent hydrochloric acid (150 ml) was added and the layers separated. The acid layer was extracted with ethyl acetate (150 ml), combined, washed with water (150 ml), dried over sodium sulfate, filtered and the solvents evaporated. The solid was taken up in hot ethyl acetate and recrystallized from hexane to yield the title compound, m.p. ca. 143.5°–145.0° C.

Analysis calc. for $C_{11}H_{13}NO$ (175.23):
Calc.: C, 75.40; H, 7.48; N, 7.99.
Found: C, 75.25; H, 7.51; N, 7.79.

EXAMPLE 7

3-[[3,5-bis(1,1-dimethylethyl)-4-hydroxyphenyl]thio]-N-(2,6-dimethylphenyl)propanamide

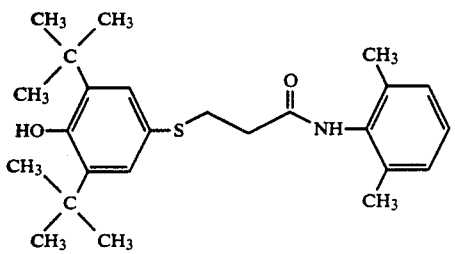

2,6-bis-(1,1-Dimethylethyl)-4-mercaptophenol(1.19 g, 0.005 mole), N-(2,6-dimethylphenyl)-2-propenamide (0.87 g, 0.005 mole) and triethylamine (0.5 ml) in methanol (100 ml) were stirred at room temperature under argon for 12 hours. The solvent and triethylamine were removed on a rotary evaporator and the product purified by chromatography on silica. The solvents were removed and the product recrystallized from ethyl acetate/hexane, filtered and dried in vacuo to yield the title compound, m.p. ca. 142.5°–144° C.

Analysis calc.: for $C_{25}H_{35}NSO_2$(413.62):
Calc.: C, 72.60; H, 8.53; S, 7.75; N, 3.39.
Found: C, 72.28; H, 8.75; S, 7.80; N, 3.37.

EXAMPLE 8

1-[3-[[3,5-Bis(1,1-dimethylethyl)4-hydroxyphenyl]thio]-1-oxopropyl]-4-(phenylmethyl)piperazine

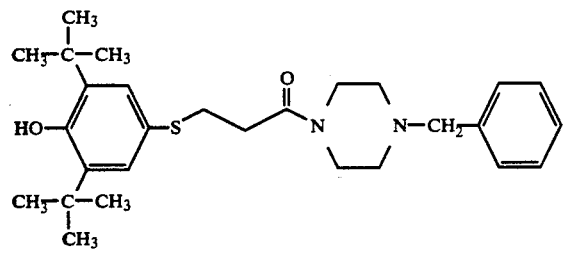

2,6-Bis-(1,1- dimethylethyl)-4-mercaptophenol (1.52 g, 0.0064 mole), 1-(1-oxo-2-propenyl)-4-phenylmethyl)-piperazine (1.47 g, 0.0064 mole) and triethylamine (0.5 ml) were dissolved in 150 ml of methanol and stirred at room temperature for 12 hours. The solvent was removed on a rotary evaporator, and the reaction chromatographed on silica gel. The product was recrystallized from ethyl acetate and hexane. The resulting white solid was filtered and dried overnight in a vacuum pistol at room temperature, m.p about 92.5°–95° C., (468.70).

Analysis calc. for $C_{28}H_{40}N_2SO_2$:
Calc.: C, 71.75; H, 8 60; N, 5.98; S, 6.84.
Found: C, 71.67; H, 8.69; N, 6.04; S, 6.87.

EXAMPLE 9

2,6-bis(1,1-dimethylethyl)-4-[(3-hydroxy-4-methylpentyl)thio]phenol

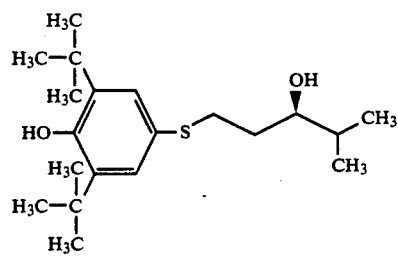

3-[[3,5-bis(1,1-dimethylethyl)-4-hydroxyphenyl]thio] propanol (2.0 g, prepared as described in U.S. Pat. No. 4,857,558) was dissolved in 20 ml of dry tetrahydrofuran under argon and added to 8.5 ml of 2 M isopropylmagnesium chloride in tetrahydrofuran that had previously been added under argon gas to a flask that had been dried in vacuo overnight. Reaction temperature was maintained at 10°–15° C. with an ice bath. When addition was complete, the reaction mixture was allowed warm to room temperature and stirred for 3 hours. 2N hydrochloric acid (2 ml) was added followed by 50 ml of water and the mixture extracted with ethyl acetate three times. The organic extracts were combined, washed with water twice and dried over sodium sulfate. The solvent was removed in vacuo after filtration and the crude product chromatographed on silica to give the title compound.

Analysis calc. for $C_{20}H_{34}O_2S$(338.54):
Calc.: C, 70.96; H, 10.12; S, 9.47.
Found: C, 71.29; H, 10.25; S, 9.43.

EXAMPLE 10

2,6-bis(1,1-dimethylethyl)-4-[(3-hydroxy-3,4-dimethylpentyl)thio]phenol

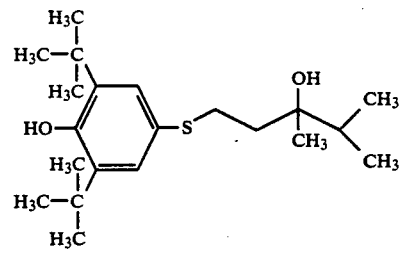

5 ml of 2.0M isopropylmagnesium bromide in tetrahydrofuran was cooled in an ice bath and a solution of 4-[[3,5-bis(1,1-dimethylethyl)-4-hydroxyphenyl]thio]-2-butanone (prepared as in U.S. Pat. No. 4,857,558) (750 mg) in tetrahydrofuran (25 ml) was added dropwise under argon and the reaction mixture treated by the method of Example 9 to give the title compound.

Analysis calc. for $C_{21}H_{36}O_2S$(352.52):
Calc.: C, 71.54; H, 10.29; S, 9.09.
Found: C, 71.44; H, 10.11; S, 9.36.

What is claimed is:

1. A method of stimulating superoxide generation which comprises administering to a mammal in need of such treatment an amount of a compound of the Formula I

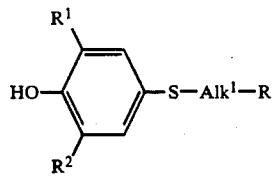
(I)

or a pharmaceutically acceptable salt or stereoisomer or geometric isomer thereof; wherein $R^1$ and $R^2$ are the same or different and independently represent tert-alkyl or phenyl; $Alk^1$ represents straight or branched chain alkylene of 1 to 10 carbon atoms; and R represents:

b)

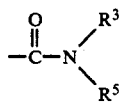

wherein $R^3$ is hydrogen or alkyl of 1 to 4 carbon atoms and $R^5$ is phenyl or substituted phenyl;

c)

wherein $R^6$ is a heterocyclic amine represented by the formula

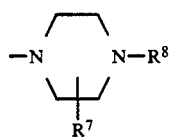

wherein $R^7$ is hydrogen or alkyl of 1 to 4 carbon atoms and $R^8$ is hydrogen, lower alkyl, phenyl, substituted phenyl, benzyl or substituted benzyl; or d)

wherein $R^9$ is hydrogen or alkyl of 1 to 4 carbon atoms and $R^{10}$ is alkyl of 1 to 10 carbon atoms; which is effective to stimulate superoxide generation.

2. A method according to claim 1 of stimulating superoxide generation which comprises administering to a mammal in need of such treatment an amount of a compound of the formula

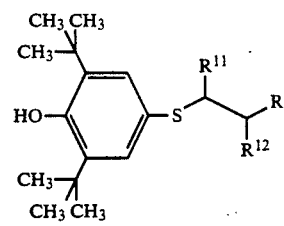

or a pharmaceutically acceptable salt or stereoisomer or geometric isomer thereof, wherein $R^{11}$ and $R^{12}$ are alike or different and are hydrogen or alkyl of 1 to 4 carbon atoms, and R represents:

b)

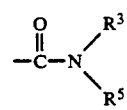

wherein $R^3$ is hydrogen or alkyl of 1 to 4 carbon atoms and $R^5$ is phenyl or substituted phenyl;

c)

wherein $R^6$ is a heterocyclic amine represented by the formula

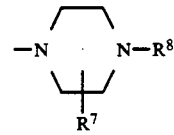

wherein $R^7$ is hydrogen or alkyl of 1 to 4 carbon atoms and $R^8$ is hydrogen, lower alkyl, phenyl, substituted phenyl, benzyl or substituted benzyl; or d)

wherein $R^9$ is hydrogen or alkyl of 1 to 4 carbon atoms and $R^{10}$ is alkyl of 1 to 10 carbon atoms; which is effective to stimulate superoxide generation.

3. A method according to claim 1 wherein said compound is 3-[[3,5-bis(1,1-dimethylethyl)-4-hydroxyphenyl]thio]-N-(2,6-dimethylphenyl)propanamide.

4. A method according to claim 1 wherein said compound is 1-[3-[[3.5-bis(1,1-dimethylethyl)4-hydroxyphenyl]thio]-1-oxopropyl]-4-(phenylmethyl)piperazine.

5. A method according to claim 1 wherein said compound is 2,6-bis(1,1-dimethylethyl)-4-[(3-hydroxy-4-methylpentyl)thio]phenol.

6. A method according to claim 1 wherein said compound is 2,6-bis(1,1-dimethylethyl)-4-[(3-hydroxy-3,4-dimethylpentyl)thio]phenol.

* * * * *

UNITED STATES PATENT AND TRADEMARK OFFICE
CERTIFICATE OF CORRECTION

PATENT NO. : 5,189,038
DATED : February 23, 1993
INVENTOR(S) : Mueller, et al.

It is certified that error appears in the above-identified patent and that said Letters Patent is hereby corrected as shown below:

Column 2, line 60, represented by the formula reading

Column 8, line 6, reading "at low" should read -- at a low --.

Column 10, line 9, reading "[[3.5" should read -- [[3,5 --.

Column 16, line 58, reading "[[3.5" should read -- [[3,5 --.

Signed and Sealed this

Twenty-fourth Day of May, 1994

Attest:

BRUCE LEHMAN

*Attesting Officer*   *Commissioner of Patents and Trademarks*